(12) United States Patent
Caimi et al.

(10) Patent No.: US 8,962,282 B2
(45) Date of Patent: *Feb. 24, 2015

(54) INCREASED POLY (ALPHA 1,3 GLUCAN) YIELD USING TETRABORATE

(71) Applicant: E I du Pont de Nemours and Company, Wilmington, DE (US)

(72) Inventors: Perry G Caimi, Kennett Square, PA (US); Susan Marie Hennessey, Avondale, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/719,260

(22) Filed: Dec. 19, 2012

(65) Prior Publication Data

US 2013/0196384 A1     Aug. 1, 2013

Related U.S. Application Data

(60) Provisional application No. 61/577,280, filed on Dec. 19, 2011.

(51) Int. Cl.
| | |
|---|---|
| *C12P 19/18* | (2006.01) |
| *C12N 9/10* | (2006.01) |
| *C12P 19/12* | (2006.01) |
| *C12P 19/44* | (2006.01) |

(52) U.S. Cl.
CPC .............. *C12P 19/18* (2013.01); *C12N 9/1048* (2013.01); *C12P 19/12* (2013.01); *C12P 19/44* (2013.01)
USPC ........................................... 435/97; 435/193

(58) Field of Classification Search
None
See application file for complete search history.

(56) References Cited

U.S. PATENT DOCUMENTS

| | | | | |
|---|---|---|---|---|
| 3,689,362 | A | * | 9/1972 | Takasaki ........................ 435/94 |
| 7,000,000 | B1 | | 2/2006 | O'Brien |
| 2012/0282659 | A1 | * | 11/2012 | Yamamoto et al. ............. 435/97 |

OTHER PUBLICATIONS

International Search Report, Corresponding International Patent Application No. PCT/US2012/070729, E. I. Du Pont De Nemours and Company, Mailed Mar. 1, 2013.
Related U.S. Appl. No. 13/719,261, Caimi et al, filed Dec. 19, 2012.
Related International Patent Application, PCT Application No. PCT/US2012/070715, E. I. Dupont De Nemours and Company, filed Dec. 19, 2012.
International Search Report, Related International Patent Application, PCT Application No. PCT/US2012/070715, E. I. Dupont De Nemours and Company, Mailed May 23, 2013.
Acree, The Chemistry of Sugars in Boric Acid Solutions, Adv. Chem, American Chemical Society: Washington, DC (1973), pp. 208-219.
Pollak et al., Calorimetric Study of the Interactions of D-Glucose, D-Fructose, Sucrose and Poly(Vinyl Alcohol) with Borate Ions, Carbohydrate Research, vol. 241 (1993), pp. 279-283.
Robyt et al., Stereochemistry Involved in the Mechanism of Action of Dextransucrase in the Synthesis of Dextran and the Formation of Acceptor Products, Bioorganic Chemistry, vol. 11 (1982), pp. 115-132.
Simpson et al., Four Glucosyltransferases, GTFJ, GTFK, GTFL, and GTFM, From *Streptococcus salivarious* ATCC 25975, Microbiology, vol. 141 (1995), pp. 1451-1460.
Valdivia et al., Dextran Synthesis in the Presence of Oxianions, Annals of the New York Academy of Sciences, Wiley-Blackwell Publishing, Inc., US., vol. 542 (1988), pp. 390-394.
Valdivia et al., Effect of Borate Ions on Dextransucrase Acceptor Reaction, Biotechnology Letters, vol. 9, No. 1 (1987), pp. 1-6.
Pelmore et al., N.M.R. Studies of Complexes Formed by D-Fructose and Borate Ions in Aqueous Solution, Carbohydrate Research, vol. 155 (1986), pp. 206-211.

* cited by examiner

*Primary Examiner* — Rebecca Prouty
*Assistant Examiner* — Richard Ekstrom

(57) ABSTRACT

A process for production of poly (α 1,3 glucan) from a renewable feedstock, for applications in fibers, films, and pulps. The effect of addition of tetraborate in increasing the yield of the desired end products, poly (α 1,3 glucan) and fructose, and decreasing formation of the undesired by-product leucrose.

8 Claims, No Drawings

INCREASED POLY (ALPHA 1,3 GLUCAN) YIELD USING TETRABORATE

CROSS-REFERENCE TO RELATED APPLICATIONS

This application claims the benefit of priority to U.S. Provisional Application No. 61/577,280, filed on Dec. 19, 2011.

FIELD OF INVENTION

This invention relates to the field of production of a polysaccharide. Specifically, it relates to production of poly (α 1,3 glucan) via an enzymatic reaction. More specifically, it relates to increasing the titer of poly (α 1,3 glucan) formed during the enzymatic reaction.

BACKGROUND

Cellulose, a polysaccharide consisting of β(1, 4)-linked glucose, formed by natural processes, (Applied Fiber Science, F. Happey, Ed., Chapter 8, E. Atkins, Academic Press, New York, 1979) has become the preeminent fiber for use in manufactured textiles, films and resins. Cotton, an especially pure form of naturally occurring cellulose, is well-known for its beneficial attributes in textile applications.

Cellulosic fibers such as cotton and rayon increasingly present sustainability issues with respect to land use and environmental imprint. This may be a significant factor leading to increased level of research into textiles containing polyester fiber blends with cellulosic materials and more sustainable solutions for cellulosic-derived materials. It is highly desirable, therefore, to discover other glucose-based polysaccharides for application in films, fibers and resins that can be economically produced from renewable resources. In addition such polymers offer materials that are environmentally benign throughout their entire life cycle.

Poly (α 1,3 glucan), a glucan polymer characterized by having α (1,3) glycoside linkages, has been isolated by contacting an aqueous solution of sucrose with a glycosyltransferase (gtfJ) enzyme isolated from *Streptococcus salivarius* (Simpson et al., Microbiology, 141: 1451-1460, 1995). Poly (α 1,3 glucan) refers to a polysaccharide composed of D-glucose monomers linked by glycosidic bonds. Films prepared from poly (α 1,3 glucan) tolerate temperatures up to 150° C. and provide an advantage over polymers obtained from β (1,4) linked polysaccharides (Ogawa et al., Fiber Differentiation Methods, 47: 353-362, 1980).

U.S. Pat. No. 7,000,000 disclosed preparation of a polysaccharide fiber comprising hexose units, wherein at least 50% of the hexose units within the polymer were linked via α (1,3) glycoside linkages using the gtfJ enzyme. The gtfJ enzyme utilizes sucrose as a substrate in a polymerization reaction producing poly (α 1,3 glucan) and fructose as end-products (Simpson et al., et al., Microbiology, 141: 1451-1460, 1995).

Production of low-cost poly (α 1,3 glucan) derived from sucrose, for commercial applications, requires a high yield process producing minimal undesirable by-products. In addition to poly (α 1,3 glucan), the other end product, fructose, is also a desirable product due to its application as a high value sweetener. However, fructose is also known to compete with glucose, acting as an acceptor in the gtf enzyme reaction thus hindering conversion of available glucose to poly (α 1,3 glucan) and limiting the final titer of poly (α 1,3 glucan) (Valdivia et al., (Ann. NY Acad. Sci. 542:390-394, 1988).

Robyt and Eklund (Bioorganic Chemistry, 11: 115-132, 1982) and Prat, D, et al., (Biotechnol. Letters, 9: 1-6, 1987) reported production of a by-product leucrose, a disaccharide of glucose and fructose with α (1,5) linkages, as well as fructose, by the dextranase enzyme of *Leuconostoc mesenteroides* when sucrose was used as substrate. Dextranase enzymes (E.C. 2.4.1.2) belong to glycosyltransferases family of enzymes and catalyze α (1,4) and α (1,6) type glycoside linkages.

Tetraborate or sodium tetraborate is a boron compound with the chemical formula: $Na_2B_4O_7$. Tetraborate may form a compact polyion by corner sharing of oxygen atoms. The polyions may exist as discrete elements or they may share additional oxygen atoms to form structural units in long chains or three-dimensional networks. Tetraborate is known to react with suitable diol containing compounds (e.g., carbohydrates) in aqueous solution, to produce borate esters (T. Acree, Adv. Chem.; Am. Chem. Soc.: Washington, DC, pp 208-219, 1973). The suitability of a diol for reaction with tetraborate is determined by Oxygen-Oxygen bond distance (2.49 A to 2.63 A) within the diol and an Oxygen-Carbon-Carbon-Oxygen dihedral angle of less than 40°. Fructose, in the furanose form, is an excellent configuration for bond distance and dihedral angle compared to glucose or sucrose for reaction with tetraborate. Thus, the equilibrium constant for ester formation with tetraborate favors fructose over glucose or sucrose in solution (Pollak, V. and Mlynek, J.; Carbohydrate Research, 241: 279-283, 1993). This relatively strong association between fructose and tetraborate can be used to sequester this carbohydrate in a solution containing other sugars. Sequestration of fructose prevents its use as an acceptor in the dextranase reaction resulting in reduced leucrose synthesis. Prat et al., (supra) and Valdivia et al., (supra) described altering the yield of end products in a dextranase reaction by adding sodium tetraborate under strict conditions including specific concentrations of sodium tetraborate (<110 mM) and at pH<7.0. In the presence of 60 mM sodium tetraborate and at pH 7.0, the dextranase enzyme used by Prat et al., (supra) showed no activity at all.

Interaction between tetraborate or borate anions occurs with carbohydrates having a specific configuration (Pollak, and Mlynek, supra). It is not clear whether a similar interaction can occur between borate and poly (α 1,3 glucan). Furthermore, it has been shown that tetraborate dramatically reduces the activity of *Leuconostoc mesenteroides* dextranase, which belongs to a family of enzymes that catalyze α (1,4) and α (1,6) type glycoside linkages. It is not known if similar effects can be observed with the general class of glycosyltransferases which produce a high percentage of α (1,3) glycosyl linkages.

Commercial production of poly (α 1,3 glucan) and fructose from sucrose, using glycosyltransferases, requires development of methods to increase the yield of these products during the enzymatic reaction.

SUMMARY OF INVENTION

This invention is a process for production of poly (α 1,3 glucan) from a renewable feedstock, for applications in fibers, films, and pulps. The effect of addition of tetraborate in increasing the yield of the desired end products and decreasing undesired by-product leucrose formation is disclosed. In one aspect, the disclosed invention is a reaction solution for the synthesis of poly (α 1,3 glucan) comprising:
   a) at least one gtf enzyme;
   b) tetraborate; and
   c) sucrose, whereby poly (α 1,3 glucan) is produced with a lower concentration of leucrose by-product than is produced in the absence of tetraborate.

In another aspect, the disclosed invention is an improved process for producing (α 1,3 glucan) having a reduced concentration of leucrose as by-product comprising the steps:
  a) providing a reaction solution comprising:
    i) at least one gtf enzyme;
    ii) tetraborate; and
    iii) sucrose;
wherein sucrose is converted by the enzyme to poly (α 1,3 glucan) and fructose and wherein the amount of leucrose produced is less than 44% of the sucrose converted.

NUCLEOTIDE SEQUENCES

SEQ ID NO. 1—is the amino acid sequence (amino acid 178 to 1518) for *Streptococcus salivarius* gtfJ (Genbank accession number Z11873).

SEQ ID NO. 2—is the coding sequence (base 532 to base 4557) for *Streptococcus salivarius* gtfJ, (Genbank accession number Z11873.

DETAILED DESCRIPTION OF INVENTION

Poly (α 1,3 glucan) is a potentially low cost polymer which can be enzymatically produced from renewable resources such as sucrose using the gtfJ enzyme of *Streptococcus salivarius*. The present invention describes formation of by-products poly (α 1,3 glucan), fructose and leucrose in gtf enzyme reactions and the effect of tetraborate in increasing fructose formation and decreasing leucrose formation.

The term "glycosyltransferase (gtf) enzyme", as used herein, refers to an enzyme excreted by oral streptococci, such as *Streptococcus salivarius* which utilizes the high free energy of the glycosidic bond of sucrose to synthesize poly (α 1,3 glucan). A glycosidic bond can join two monosaccharides to form a disaccharide. The glycosidic bonds can be in the α or β configuration and can generate, for example, α (1,2), α (1,3), α (1,4), α (1,6), β (1,2), β (1,3), β (1,4) or β (1,6) linkages. The term "α (1,3) glycoside linkage", as used herein, refers to a type of covalent bond that joins glucose molecules to each other through the ring carbons 1 and 3 on adjacent glucose rings.

The term "poly (α 1,3 glucan)", as used herein, refers to high molecular weight, linear polymers obtained from polysaccharide molecules resulting from linking glucose units via α (1,3) glycosidic linkages.

The present invention relates to a process for increasing the titer of the polysaccharide, poly (α 1,3 glucan) and fructose and decreasing the titer of the undesired by-product, leucrose, in an enzymatic reaction solution using sucrose as the substrate and one or more gtf enzymes. The term "enzymatic reaction" refers to a reaction that is performed by the gtf enzyme. An "enzyme reaction solution" of the present invention generally refers to a reaction mixture comprising at least one gtf enzyme in a buffer solution comprising sucrose and possibly one or more primers to convert sucrose to poly (α 1,3 glucan).

The glycosyltransferase enzyme used in the present invention can be any gtf enzyme. The gtf enzyme used can be from any streprococci. Suitable gtf enzymes can be, for example, the gtfJ of *Streptococcus salivarius*, the gtfB and the gtfC from *Streptococcus mutans*, the gtfI of *Streptococcus sobrinus*, and the gtfI from *Streptococcus downei*. Particularly, the *Streptococcus* species can be *Streptococcus salivarius*. More particularly, the gtf enzyme can be the gtfJ (E.C. 2.4.1.5) enzyme of *Streptococcus salivarius*. Alternatively, the gtfI enzyme of Streptococcus sobrinus can be used.

In one embodiment, the enzyme reaction solution can comprise only one gtf enzyme as described herein. In another embodiment, the enzyme reaction solution can comprise a combination of more than one type of gtf enzyme.

For purposes of this invention, sufficient quantities of the gtfJ enzyme can be produced using a recombinant *E. coli* strain expressing the desired gtfJ enzyme. Methods for designing the codon optimized genes and expression in *E. coli* are well known in the art. The *E. coli* strain (DH10B) expressing gtfJ enzyme was prepared as described in the commonly owned U.S. Pat. No. 7,000,000.

Methods for the growth of recombinant microorganisms are well known in the art. Recombinant microorganisms expressing the desired gtf enzyme to perform the instant reaction can be grown in any container, such as, for example: various types of flasks with and without indentations; any container that can be sterilized and sealed and temperature-controlled; or any type of fermenter. In one embodiment, production of the gtfJ enzyme for poly (α 1,3 glucan) production in the present invention can be achieved by growing the recombinant *E. coli* DH10B, expressing the gtfJ enzyme, in a fermenter.

The gtfJ enzyme of *Streptococcus salivarius*, used as the catalyst for conversion of sucrose to poly (α 1,3 glucan) in the current invention, is a primer-dependent gtf enzyme. A primer-dependent gtf enzyme as referenced in the present application refers to a gtf enzyme that requires the presence of an initiating molecule in the enzyme reaction solution to act as a primer for the enzyme during poly (α 1,3 glucan) synthesis. Thus a "primer", as the term is used herein, refers to any molecule that can act as the initiator for the primer-dependent glycosyltransferases. Many other glycosyltransferases are primer-independent enzymes. The primer-independent enzymes do not require the presence of a primer to perform the reaction. For the purposes of the present invention, either or both a primer-independent enzyme, and/or a primer-dependent gtf enzyme can be used in the same enzyme reaction system during poly (α 1,3 glucan) synthesis.

The gtfJ is a primer-dependent enzyme. In the present invention, dextran, which is a complex, branched glucan was used as a primer for the gtfJ enzyme. While gtfJ is a primer-dependent enzyme, conversion of sucrose to poly (α 1,3 glucan) with this enzyme can also occur in the absence of a primer.

In addition to dextran other carbohydrate-based primers can be used in the gtf reaction of the current invention. In one embodiment, the primer can be from any low to med molecular weight (2,000-50,000 Dalton) glucose-based carbohydrate.

In another embodiment, the primer in the reaction solution can be hydrolyzed poly (α 1,3 glucan). In another embodiment, the primer in the reaction solution can be from any low to med (2,000-50,000 Dalton) non-glucose-based carbohydrate. In another embodiment, the primer in the reaction solution can be from any combination of any low to med molecular weight glucose-based carbohydrate. In another embodiment, the primer is glucose.

The production of poly (α 1,3 glucan), by the gtfJ enzyme of *Streptococcus salivarius*, is inhibited by its end product, fructose. When fructose accumulates in the enzyme reaction solution it can inhibit poly (α 1,3 glucan) production, presumably by competing for available glycosyl moieties and thus results in the formation of the undesirable by-product disaccharide, leucrose.

Tetraborate can be used to sequester fructose in a solution containing other sugars. The sequestration of fructose prevents its use as an acceptor in the gtf reaction and therefore results in reduced leucrose synthesis. The term "sequestration of fructose", as used herein, refers to formation of a tight association between fructose and tetraborate thus preventing fructose from reacting with gtf to produce the undesirable by-product, leucrose.

In one embodiment, the yield from sucrose can be increased by decreasing the formation of leucrose to less than 42% of the amount of leucrose formed in the absence of tetraborate. In another embodiment, the amount of leucrose formed in the presence of tetraborate can be less than one-half the amount of leucrose formed in the absence of tetraborate. In still another embodiment, the amount of leucrose formed in the presence of tetraborate can be less than one-third the amount formed in the absence of tetraborate. In still another embodiment, the amount of leucrose formed in the presence of tetraborate can be less than one-tenth the amount formed in the absence of tetraborate.

In one embodiment, the concentration of tetraborate used in the gtfJ reaction mixture can be from 100 millimolar (mM) to 150 mM.

In another embodiment the concentration of poly ($\alpha$ 1,3 glucan) in the enzymatic reaction solution is increased from 0.18 grams poly ($\alpha$ 1,3 glucan) per gram of sucrose to 0.30 grams poly ($\alpha$ 1,3 glucan) per gram of sucrose.

Other materials that can be used in place of tetraborate to sequester fructose can include, but may not be limited to: 2-Aminopyrimidine-5-boronic acid; Benzene-1,4-diboronic acid; Carboxyphenylboronic acid; Fluorene-2-boronic acid; Furan-2-boronic acid; Naphthalene-1-boronic acid; Nitrophenylboronic acid; n-Pentylboronic acid; Methylpropylboronic acid;

Methoxyphenylboronic acid; and Phenylboronic acid, for example. In the practice of the present invention, the pH of the gtf enzyme reaction solution can be from 6.85 to 7.75. In one embodiment the pH of the gtf enzyme reaction solution is 6.85. In another embodiment, the pH of the gtf enzyme reaction solution is 7.75.

EXAMPLES

The invention is further described but not limited by the following specific embodiments thereof.

Materials

T10 dextran (D9260), Isopropyl β-D-1-thiogalactopyranoside (IPTG) (16758) and sodium tetraborate (B9876) were obtained from Sigma, St. Louis, Mo.

Whatman-1 filter paper was obtained from Whatman Filters, Maidstone Kent, UK.

Solenoid driven micro-valve was from Bio-Chem Fluidics, Boonton, N.J.

BellCo spin flask was from Bellco, Vineland, N.J.

VWR Ag/AgCL pH probe was from VWR International, Radnor, Pa.

Eutech pH/ORP controller was from division of Thermo Fisher Scientific Inc., Waltham, Mass.

The bead beater was obtained from MP Biomedicals, Eschwege, Germany).

Eppendorf 5415D Centrifuge was from Eppendorf, Hamburg, Germany)

Protein concentration in samples were determined using the Coomassie Plus, Bradford Assay Kit (Thermo Scientific, Rockford, Ill.)

High pressure chromatography (HPLC) was performed using a 1200 series, Agilent, Santa Clara Calif.) instrument. The column used for analysis was an Aminex HPX-87C column, (Bio-Rad Laboratories, Hercules, Calif.) which was maintained at 85° C. using a flow rate of 0.6 milliliters per minute (mL/min) with water as the mobile phase. HPLC analysis was used to determine disappearance of sucrose and the accumulation of fructose, glucose and leucrose. Using this system the following retention times were observed for chemicals of interest: sucrose (8.29 minutes, min); leucrose (9.40 min); glucose (10.12 min) and fructose (12.89 min).

Luria broth (LB) medium was from Becton, Dickinson and Company, Franklin Lakes, N.J.

Example 1

Preparation of Crude Extracts of Gtfj

The gtfJ gene of *S. salivarius* is available in Genbank (Genbank accession number Z11873, SEQ ID NO. 1). To produce sufficient quantities of gtfJ, a truncated gtfJ gene (SEQ ID NO. 2) was expressed in *E. coli* strain (DH10B) as described in the commonly owned U.S. Pat. No. 7,000,000. *E. coli* (DH10B), cells expressing the gtfJ enzyme, were grown in the LB medium (10 grams per liter, g/L Tryptone; 5 g/L yeast extract; and 10 g/L NaCl). *E. coli* cells were inoculated to an initial optical density (OD at $600_{nm}$) of 0.025 and were allowed to grow at 37° C. in an incubator while shaking at 250 rpm. The cultures were then induced by addition of 1 mM IPTG when they reached an OD of 0.8-1.0. Induced cultures were left on the shaker and harvested 3 hours post induction. The cells were removed by centrifugation (25° C., 16,000 rpm) using an Eppendorf centrifuge and cell pellets were suspended in 0.01 volume of 5.0 mM phosphate buffer (pH 7.0) and cooled to 4° C. on ice. The cells were broken using a bead beater with 0.1 millimeters (mm) silica beads. The broken cells were centrifuged at 16,000 rpm at 4° C. to precipitate the unbroken cells and cell debris. The crude extract (containing soluble gtfJ enzyme) thus obtained contained 1.64 milligram per milliliter (mg/mL) of protein as determined by the Bradford protein assay.

Example 2

Effect of Tetraborate Addition on the Amount of Product Formed by GTFJ

To determine the effect of tetraborate addition on the level of by-product accumulation, enzyme reactions were performed in 50 mL reactors in the presence (test) or absence (control) of sodium tetraborate.

GtfJ reaction solutions contained sucrose (100-150 grams per liter, g/L); potassium phosphate buffer (10 millimolar, mM); T10-dextran primer at a final concentration of 1 g/L; and total soluble enzyme (0.4-1.0 volume percent, %). Reactions were performed at 25° C.-35° C. in the presence or absence of tetraborate. Concentration of sucrose, leucrose, fructose and glucose were determined using high HPLC.

A stationary reaction was conducted containing a solution of: sucrose (100g/L); gtfJ enzyme (0.4 volume %) and T-10 dextran primer (1g/L). The initial pH of the reaction solution was adjusted to 7.5 using phosphate buffer. The temperature was held at 30° C. for 46 hours.

Tetraborate at a final concentration of 150 mM was added to the reaction solution and the pH was adjusted to 7.5 using sodium hydroxide, prior to gtfJ enzyme addition. The pH of the reaction solution was monitored throughout the test, but was not adjusted. The pH of the reaction containing tetraborate dropped from the initial adjusted pH to a final of 6.01, while the control reaction without tetraborate, did not change throughout the experiment.

Addition of tetraborate at a final concentration of 150 mM into the reaction containing *S. salivarius* gtf-J enzyme solution resulted in a decrease of the by-product leucrose by a factor of over 2.5-fold (Table 1). Additionally, the yield of α 1,3 glucan and fructose increased in the reaction containing tetraborate.

TABLE 1

Effect of tetraborate on gtfJ reaction by-product accumulation

| Grams/liter | Control | 150 mM Tetraborate |
|---|---|---|
| Initial Sucrose | 106.07 | 111.19 |
| End sucrose | 12.15 | 9.22 |
| leucrose | 39.21 | 15.52 |
| glucose | 7.55 | 13.80 |
| fructose | 29.52 | 44.63 |
| % sucrose used | 89 | 91 |
| Leucrose (% of sucrose) | 42 | 15 |
| Glucose (% of sucrose) | 8 | 14 |
| Fructose (% of sucrose) | 31 | 44 |
| Yield g poly(α1,3 glucan)/ g sucrose) | 0.16 | 0.27 |

Example 3

Effect Tetraborate Addition on the Concentration of By-Product Formed and Rate of Sucrose Use To determine the effect of tetraborate addition on the rate of sucrose conversion and on the level of by-product accumulation, enzyme reactions were performed in 50 mL reactors in the presence (test) or absence (control) of sodium tetraborate.

A reaction was conducted containing a solution of: sucrose (100g/L); gtfJ enzyme (0.4 volume %) and T-10 dextran primer (1 g/L). The initial pH of the reaction solution was adjusted to 6.85 using phosphate buffer. The temperature was held at 30° C. Samples for HPLC analysis were collected at 0, 24 and 46 hours. Tetraborate at a final concentration of 100 mM was added to the reaction solution and the pH was adjusted to 6.85 using sodium hydroxide, prior to gtfJ enzyme addition. The pH of the reaction solution was monitored throughout the test, but was not adjusted.

Addition of tetraborate at a final concentration of 100 mM into the reaction containing *S. salivarius* gtf-J enzyme solution resulted in an increased rate of sucrose consumption and decreased accumulation of the by-product leucrose by a factor of over 1.6-fold (Table 2). Additionally, the yield of fructose increased proportionally in the reaction containing tetraborate.

TABLE 2

Effect of tetraborate on gtfJ reaction rate and by-product accumulation

| | 24 Hours | | 46 Hours | |
|---|---|---|---|---|
| Grams/liter | Control | 100 mM Tetraborate | Control | 100 mM Tetraborate |
| Initial Sucrose | 101.59 | 103.99 | | |
| End sucrose | 35.98 | 6.26 | 12.15 | 4.89 |
| leucrose | 27.17 | 24.29 | 39.21 | 24.32 |
| glucose | 7.22 | 9.70 | 7.55 | 9.76 |
| fructose | 23.34 | 41.31 | 29.52 | 41.43 |
| % sucrose used | 65 | 94 | 88 | 95 |
| Leucrose (% of sucrose) | 41 | 25 | 44 | 25 |
| Glucose (% of sucrose) | 11 | 10 | 8 | 10 |
| Fructose (% of sucrose) | 36 | 42 | 33 | 42 |

Example 4

Effect Tetraborate Addition on The Concentration of By-Product Formed by Gtfj in a Ph Controlled Reaction To determine the effect of tetraborate in a pH controlled reaction, a 150 ml capacity Bellco spin flask was used and pH of the reaction solution was monitored using a VWR Ag/AgCL pH probe which was linked to a Eutech pH/ORP controller set to maintain pH at 7.75. Base was delivered to the reaction using a solenoid driven micro-valve from a reservoir containing 2M sodium hydroxide. The gtfJ reaction solutions contained: sucrose (120 g/L); gtfJ (0.5 volume %), T-10 dextran primer (1 g/L) and tetraborate at 100 mM or no tetraborate as a control reaction. The reactions were run at 25° C. for 66 hours.

The data shown in Table 3 compares sucrose consumption and product synthesis in gtfJ enzyme reaction solutions, containing 100 mM tetraborate, with the control. The pH of the control reaction was monitored and found not to change through the duration of the experiment. The level of leucrose at the conclusion of the experiment was approximately 9-fold lower when tetraborate was present, compared to the control. Additionally, the yield of α 1,3 glucan increased in the reaction containing tetraborate. The level of fructose was also increased in the presence of tetraborate.

TABLE 3

Effect of tetraborate on pH controlled gtfJ reaction product formation

| Grams/liter | Control | 100 mM Tetraborate |
|---|---|---|
| Initial Sucrose | 119.11 | 120.18 |
| End sucrose | 25.08 | 13.99 |
| Leucrose | 41.33 | 4.35 |
| Glucose | 6.88 | 15.29 |
| Fructose | 31.04 | 43.67 |
| % Sucrose used | 79 | 88 |
| Leucrose (% of sucrose) | 44 | 4 |
| Glucose (% of sucrose) | 7 | 14 |
| Fructose (% of sucrose) | 33 | 41 |
| Yield g poly(α1,3 glucan)/ g sucrose) | 0.18 | 0.30 |

What is claimed is:

1. A reaction solution for the synthesis of poly (alpha 1,3 glucan) comprising:
    a) at least one *Streptococcus* glucosyltransferase enzyme that synthesizes poly (alpha 1,3 glucan) from sucrose, wherein said glucosyltransferase enzyme comprises SEQ ID NO:1;
    b) tetraborate at a concentration from about 100 millimolar to about 150 millimolar; and
    c) sucrose,
    wherein the reaction solution pH is maintained from 6.85 to 7.75,
    whereby poly (alpha 1,3 glucan) is produced with a lower concentration of leucrose by-product than is produced in the absence of tetraborate.

2. The reaction solution of claim 1, further comprising at least one primer.

3. The reaction solution of claim 2, wherein the primer is dextran.

4. The reaction solution of claim 2, wherein the primer is hydrolyzed poly (alpha 1,3 glucan).

5. The reaction solution of claim 1, wherein the yield of poly (alpha 1,3 glucan) formed in the reaction solution improves from 0.16 g glucan/g sucrose to 0.30 g glucan/g sucrose.

6. A process for reducing the amount of byproduct leucrose formed during enzymatic synthesis of poly (alpha 1,3 glucan) comprising:
    providing a reaction solution comprising:
        i) at least one *Streptococcus* glucosyltransferase enzyme that synthesizes poly (alpha 1,3 glucan) from sucrose, wherein said glucosyltransferase enzyme comprises SEQ ID NO:1;
        ii) tetraborate at a concentration from about 100 millimolar to about 150 millimolar; and
        iii) sucrose;
    wherein the reaction solution pH is maintained from 6.85 to 7.75,
    wherein the sucrose is converted to poly (alpha 1,3 glucan) and fructose and wherein the amount of leucrose formed in the conversion is less than 44% of sucrose converted.

7. The process of claim 6, wherein the yield of leucrose formed decreases from 44% sucrose to 4% of sucrose converted.

8. The process of claim 6, wherein the yield of fructose increases from 31% sucrose to 44% of sucrose converted.

* * * * *

SEQUENCE LISTING

<160> NUMBER OF SEQ ID NOS: 2

<210> SEQ ID NO 1
<211> LENGTH: 1342
<212> TYPE: PRT
<213> ORGANISM: Streptococcus salivarius

<400> SEQUENCE: 1

```
Met Asn Ile Asp Gly Lys Tyr Tyr Val Asn Glu Asp Gly Ser His
1               5                   10                  15

Lys Glu Asn Phe Ala Ile Thr Val Asn Gly Gln Leu Leu Tyr Phe Gly
                20                  25                  30

Lys Asp Gly Ala Leu Thr Ser Ser Thr Tyr Ser Phe Thr Pro Gly
            35                  40                  45

Thr Thr Asn Ile Val Asp Gly Phe Ser Ile Asn Asn Arg Ala Tyr Asp
    50                  55                  60

Ser Ser Glu Ala Ser Phe Glu Leu Ile Asp Gly Tyr Leu Thr Ala Asp
65                  70                  75                  80

Ser Trp Tyr Arg Pro Ala Ser Ile Ile Lys Asp Gly Val Thr Trp Gln
                85                  90                  95

Ala Ser Thr Ala Glu Asp Phe Arg Pro Leu Leu Met Ala Trp Trp Pro
                100                 105                 110

Asn Val Asp Thr Gln Val Asn Tyr Leu Asn Tyr Met Ser Lys Val Phe
                115                 120                 125

Asn Leu Asp Ala Lys Tyr Ser Ser Thr Asp Lys Gln Glu Thr Leu Lys
                130                 135                 140

Val Ala Ala Lys Asp Ile Gln Ile Lys Ile Glu Gln Lys Ile Gln Ala
145                 150                 155                 160

Glu Lys Ser Thr Gln Trp Leu Arg Glu Thr Ile Ser Ala Phe Val Lys
                165                 170                 175

Thr Gln Pro Gln Trp Asn Lys Glu Thr Glu Asn Tyr Ser Lys Gly Gly
                180                 185                 190

Gly Glu Asp His Leu Gln Gly Gly Ala Leu Leu Tyr Val Asn Asp Ser
                195                 200                 205

Arg Thr Pro Trp Ala Asn Ser Asp Tyr Arg Arg Leu Asn Arg Thr Ala
            210                 215                 220

Thr Asn Gln Thr Gly Thr Ile Asp Lys Ser Ile Leu Asp Glu Gln Ser
225                 230                 235                 240

Asp Pro Asn His Met Gly Gly Phe Asp Phe Leu Leu Ala Asn Asp Val
                245                 250                 255

Asp Leu Ser Asn Pro Val Val Gln Ala Glu Gln Leu Asn Gln Ile His
                260                 265                 270

Tyr Leu Met Asn Trp Gly Ser Ile Val Met Gly Asp Lys Asp Ala Asn
                275                 280                 285

Phe Asp Gly Ile Arg Val Asp Ala Val Asp Asn Val Asp Ala Asp Met
                290                 295                 300

Leu Gln Leu Tyr Thr Asn Tyr Phe Arg Glu Tyr Tyr Gly Val Asn Lys
305                 310                 315                 320

Ser Glu Ala Asn Ala Leu Ala His Ile Ser Val Leu Glu Ala Trp Ser
                325                 330                 335

Leu Asn Asp Asn His Tyr Asn Asp Lys Thr Asp Gly Ala Ala Leu Ala
                340                 345                 350

Met Glu Asn Lys Gln Arg Leu Ala Leu Leu Phe Ser Leu Ala Lys Pro
                355                 360                 365
```

-continued

```
Ile Lys Glu Arg Thr Pro Ala Val Ser Pro Leu Tyr Asn Asn Thr Phe
    370                 375                 380

Asn Thr Thr Gln Arg Asp Glu Lys Thr Asp Trp Ile Asn Lys Asp Gly
385                 390                 395                 400

Ser Lys Ala Tyr Asn Glu Asp Gly Thr Val Lys Gln Ser Thr Ile Gly
                405                 410                 415

Lys Tyr Asn Glu Lys Tyr Gly Asp Ala Ser Gly Asn Tyr Val Phe Ile
            420                 425                 430

Arg Ala His Asp Asn Asn Val Gln Asp Ile Ile Ala Glu Ile Ile Lys
        435                 440                 445

Lys Glu Ile Asn Pro Lys Ser Asp Gly Phe Thr Ile Thr Asp Ala Glu
450                 455                 460

Met Lys Gln Ala Phe Glu Ile Tyr Asn Lys Asp Met Leu Ser Ser Asp
465                 470                 475                 480

Lys Lys Tyr Thr Leu Asn Asn Ile Pro Ala Ala Tyr Ala Val Met Leu
                485                 490                 495

Gln Asn Met Glu Thr Ile Thr Arg Val Tyr Tyr Gly Asp Leu Tyr Thr
                500                 505                 510

Asp Asp Gly His Tyr Met Glu Thr Lys Ser Pro Tyr Tyr Asp Thr Ile
            515                 520                 525

Val Asn Leu Met Lys Ser Arg Ile Lys Tyr Val Ser Gly Gln Ala
530                 535                 540

Gln Arg Ser Tyr Trp Leu Pro Thr Asp Gly Lys Met Asp Asn Ser Asp
545                 550                 555                 560

Val Glu Leu Tyr Arg Thr Asn Glu Val Tyr Thr Ser Val Arg Tyr Gly
                565                 570                 575

Lys Asp Ile Met Thr Ala Asn Asp Thr Glu Gly Ser Lys Tyr Ser Arg
            580                 585                 590

Thr Ser Gly Gln Val Thr Leu Val Ala Asn Asn Pro Lys Leu Asn Leu
        595                 600                 605

Asp Gln Ser Ala Lys Leu Asn Val Glu Met Gly Lys Ile His Ala Asn
    610                 615                 620

Gln Lys Tyr Arg Ala Leu Ile Val Gly Thr Ala Asp Gly Ile Lys Asn
625                 630                 635                 640

Phe Thr Ser Asp Ala Asp Ala Ile Ala Ala Gly Tyr Val Lys Glu Thr
                645                 650                 655

Asp Ser Asn Gly Val Leu Thr Phe Gly Ala Asn Asp Ile Lys Gly Tyr
            660                 665                 670

Glu Thr Phe Asp Met Ser Gly Phe Val Ala Val Trp Val Pro Val Gly
        675                 680                 685

Ala Ser Asp Asn Gln Asp Ile Arg Val Ala Pro Ser Thr Glu Ala Lys
    690                 695                 700

Lys Glu Gly Glu Leu Thr Leu Lys Ala Thr Glu Ala Tyr Asp Ser Gln
705                 710                 715                 720

Leu Ile Tyr Glu Gly Phe Ser Asn Phe Gln Thr Ile Pro Asp Gly Ser
                725                 730                 735

Asp Pro Ser Val Tyr Thr Asn Arg Lys Ile Ala Glu Asn Val Asp Leu
            740                 745                 750

Phe Lys Ser Trp Gly Val Thr Ser Phe Glu Met Ala Pro Gln Phe Val
        755                 760                 765

Ser Ala Asp Asp Gly Thr Phe Leu Asp Ser Val Ile Gln Asn Gly Tyr
    770                 775                 780
```

-continued

Ala Phe Ala Asp Arg Tyr Asp Leu Ala Met Ser Lys Asn Asn Lys Tyr
785             790             795             800

Gly Ser Lys Glu Asp Leu Arg Asp Ala Leu Lys Ala Leu His Lys Ala
            805             810             815

Gly Ile Gln Ala Ile Ala Asp Trp Val Pro Asp Gln Ile Tyr Gln Leu
            820             825             830

Pro Gly Lys Glu Val Val Thr Ala Thr Arg Thr Asp Gly Ala Gly Arg
            835             840             845

Lys Ile Ala Asp Ala Ile Ile Asp His Ser Leu Tyr Val Ala Asn Ser
            850             855             860

Lys Ser Ser Gly Lys Asp Tyr Gln Ala Lys Tyr Gly Gly Glu Phe Leu
865             870             875             880

Ala Glu Leu Lys Ala Lys Tyr Pro Glu Met Phe Lys Val Asn Met Ile
            885             890             895

Ser Thr Gly Lys Pro Ile Asp Asp Ser Val Lys Leu Lys Gln Trp Lys
            900             905             910

Ala Glu Tyr Phe Asn Gly Thr Asn Val Leu Glu Arg Gly Val Gly Tyr
            915             920             925

Val Leu Ser Asp Glu Ala Thr Gly Lys Tyr Phe Thr Val Thr Lys Glu
930             935             940

Gly Asn Phe Ile Pro Leu Gln Leu Thr Gly Lys Glu Lys Val Ile Thr
945             950             955             960

Gly Phe Ser Ser Asp Gly Lys Gly Ile Thr Tyr Phe Gly Thr Ser Gly
            965             970             975

Thr Gln Ala Lys Ser Ala Phe Val Thr Phe Asn Gly Asn Thr Tyr Tyr
            980             985             990

Phe Asp Ala Arg Gly His Met Val  Thr Asn Ser Glu Tyr  Ser Pro Asn
            995             1000            1005

Gly Lys  Asp Val Tyr Arg Phe  Leu Pro Asn Gly Ile  Met Leu Ser
    1010            1015           1020

Asn Ala  Phe Tyr Ile Asp Ala  Asn Gly Asn Thr Tyr  Leu Tyr Asn
    1025            1030           1035

Ser Lys  Gly Gln Met Tyr Lys  Gly Gly Tyr Thr Lys  Phe Asp Val
    1040            1045           1050

Ser Glu  Thr Asp Lys Asp Gly  Lys Glu Ser Lys Val  Val Lys Phe
    1055            1060           1065

Arg Tyr  Phe Thr Asn Glu Gly  Val Met Ala Lys Gly  Val Thr Val
    1070            1075           1080

Ile Asp  Gly Phe Thr Gln Tyr  Phe Gly Glu Asp Gly  Phe Gln Ala
    1085            1090           1095

Lys Asp  Lys Leu Val Thr Phe  Lys Gly Lys Thr Tyr  Tyr Phe Asp
    1100            1105           1110

Ala His  Thr Gly Asn Gly Ile  Lys Asp Thr Trp Arg  Asn Ile Asn
    1115            1120           1125

Gly Lys  Trp Tyr Tyr Phe Asp  Ala Asn Gly Val Ala  Ala Thr Gly
    1130            1135           1140

Ala Gln  Val Ile Asn Gly Gln  Lys Leu Tyr Phe Asn  Glu Asp Gly
    1145            1150           1155

Ser Gln  Val Lys Gly Gly Val  Val Lys Asn Ala Asp  Gly Thr Tyr
    1160            1165           1170

Ser Lys  Tyr Lys Glu Gly Phe  Gly Glu Leu Val Thr  Asn Glu Phe
    1175            1180           1185

-continued

| | | | | | | | | | | | |
|---|---|---|---|---|---|---|---|---|---|---|---|
| Phe | Thr | Thr | Asp | Gly | Asn | Val | Trp | Tyr | Tyr | Ala | Gly | Ala | Asn | Gly |
| | 1190 | | | | 1195 | | | | 1200 | | |

Phe Thr Thr Asp Gly Asn Val Trp Tyr Tyr Ala Gly Ala Asn Gly
     1190               1195               1200

Lys Thr Val Thr Gly Ala Gln Val Ile Asn Gly Gln His Leu Tyr
    1205               1210               1215

Phe Asn Ala Asp Gly Ser Gln Val Lys Gly Gly Val Val Lys Asn
    1220               1225               1230

Ala Asp Gly Thr Tyr Ser Lys Tyr Asn Ala Ser Thr Gly Glu Arg
    1235               1240               1245

Leu Thr Asn Glu Phe Phe Thr Thr Gly Asp Asn Asn Trp Tyr Tyr
    1250               1255               1260

Ile Gly Ala Asn Gly Lys Ser Val Thr Gly Glu Val Lys Ile Gly
    1265               1270               1275

Asp Asp Thr Tyr Phe Phe Ala Lys Asp Gly Lys Gln Val Lys Gly
    1280               1285               1290

Gln Thr Val Ser Ala Gly Asn Gly Arg Ile Ser Tyr Tyr Tyr Gly
    1295               1300               1305

Asp Ser Gly Lys Arg Ala Val Ser Thr Trp Ile Glu Ile Gln Pro
    1310               1315               1320

Gly Val Tyr Val Tyr Phe Asp Lys Asn Gly Leu Ala Tyr Pro Pro
    1325               1330               1335

Arg Val Leu Asn
    1340

<210> SEQ ID NO 2
<211> LENGTH: 4049
<212> TYPE: DNA
<213> ORGANISM: Streptococcus salivarius

<400> SEQUENCE: 2

```
gggaattcca tatgaacatt gatggtaaat attactatgt taatgaagat ggttcacaca      60
aagaaaactt tgccattact gtaaatggtc aattgcttta cttcggtaaa gatggtgctc     120
ttacaagttc atcaacatac tctttcacac caggaacaac aaatattgtt gatggtttct     180
caataaataa ccgtgcctac gattcatctg aagctagctt tgaattgatt gatggttatt     240
tgactgcaga tagctggtac cgtccagctt ctatcatcaa agatggtgta acttggcaag     300
catcaactgc agaagatttc cgtccacttt tgatggcttg gtggccaaat gtagatacac     360
aagttaacta cttgaactac atgtctaaag tatttaactt ggatgctaaa tattcaagta     420
cagataagca agaaactttg aaagttgctg ctaaggacat tcaaatcaag attgagcaaa     480
agattcaggc tgaaaaatca acacaatggt tgcgtgaaac tatctctgcc tttgttaaga     540
cacaaccaca atggaacaaa gaaactgaaa actactctaa aggtggcggc gaagatcacc     600
ttcaaggtgg tgcccttctt tatgtgaatg attcacgtac accatgggcg aattctgact     660
atcgtcgttt gaaccgtaca gcaactaacc agactggtac aattgataaa tcaattcttg     720
atgagcaatc agatccaaac cacatgggtg gtttcgactt cttgctagct aatgacgtag     780
atttgtcaaa cccagttgtt caagcggaac aattgaacca aatccactac cttatgaact     840
ggggttcaat cgttatgggt gacaaggatg ctaacttcga tggtatccgt gtcgacgcgg     900
tagataatgt cgatgcagac atcttcaact ctacacaaac tacttccgtg agtactatgg     960
tgttaacaaa tctgaagcaa acgctcttgc tcacatctca gtccttgaag catggagcct    1020
taatgacaac cactacaatg acaagacaga tggcgctgcg cttgctatgg aaaacaaaca    1080
acgtttggct ctcctcttct cattggctaa accaatcaaa gaacgtacac cagctgtaag    1140
```

```
tcctttgtat aacaatactt tcaacacgac acaacgtgat gaaaagactg attggattaa    1200
caaagatgga agcaaggcct ataacgaaga cggaacagtt aaacagtcta caatcggtaa    1260
atataacgag aaatacggag atgcgtcagg aaattacgtc tttatccgtg cccatgataa    1320
caacgttcaa gatattattg ctgaaatcat caagaaagaa atcaatccaa aatcagatgg    1380
tttcacgatt actgatgctg aaatgaagca agcctttgag atttacaaca aagacatgct    1440
cagcagcgac aaaaaatata cgcttaacaa catcccagcg gcttacgcgg ttatgttgca    1500
aaacatggaa actatcactc gtgtctacta tggagaccct tatacagatg atggtcacta    1560
catggaaact aagtctccat attacgatac cattgttaac ttgatgaaga gtcgtatcaa    1620
gtatgtatct ggtgggcaag cacaacgttc atactggttg ccaactgatg gtaagatgga    1680
caattcagat gttgaacttt accgcacaaa tgaagtctac acttcagtac gttatggtaa    1740
agacattatg acagctaatg atacagaagg ttctaaatac agccgtactt ctggtcaggt    1800
aacacttgta gctaacaatc caaaattgaa tttggatcaa tcagctaaac ttaatgttga    1860
aatgggtaaa atccatgcca accaaaaata ccgtgctttg attgttggta cagctgatgg    1920
tatcaagaac tttacatctg atgcagatgc aatcgcagca ggttacgtta agaaaacaga    1980
cagcaacggt gtcttgactt tcggtgctaa tgacatcaag ggttatgaaa catttgatat    2040
gtctggtttc gtagcagttt gggttccagt tggagcttca gataatcaag atatccgagt    2100
agcgccttca acagaagcta aaaagaggg tgaattgact cttaaagcga ctgaagctta    2160
tgattcacaa ttaatctacg aaggcttctc taactttcaa actattccag atggttcaga    2220
tccttcagtc tatactaacc gtaagattgc tgaaaatgtt gatttgttca aatcatgggg    2280
tgtaacatca tttgaaatgg cacctcaatt tgtatctgct gacgatggta ccttccttga    2340
ctcagttatc caaaatggtt atgccttttgc agaccgttac gatcttgcca tgagtaagaa    2400
caataaatac ggttctaaag aagatctacg tgatgctctt aaagcacttc ataaggctgg    2460
tattcaagca atcgctgact gggttccaga ccaaatttac caattgccag gtaaagaagt    2520
tgtaacagcg actcgtactg atggtgctgg tcgtaagatt gcggacgcta tcattgacca    2580
ctcactttat gtggctaact ctaagtcatc aggcaaagat taccaagcta atacggtgg    2640 tgaattcttg gctgaactta agctaagta ccctgaaatg ttcaaggtaa acatgatttc    2700
aactggtaaa ccaattgatg attctgttaa attgaaacaa tggaaggctg aatacttcaa    2760
cggaacaaac gttcttgaac gtggtgttgg ctatgtactt agcgatgaag caactggtaa    2820
gtatttcact gtcactaaag aaggtaactt cattcctctt caattgacag gtaaagaaaa    2880
ggttattact ggattctcaa gtgatggtaa aggaatcact tacttcggta caagtggtac    2940
acaagctaaa tctgccttttg taaccttcaa tggtaacact tactactttg atgctcgtgg    3000
tcacatggtt actaacagtg aatactcacc aaatggtaaa gacgtttatc gtttcttacc    3060
aaatggtatc atgttgagta atgccttcta cattgatgct aatggtaata cctacctta    3120 taactctaaa ggtcaaatgt acaagggtgg ttacactaaa tttgatgttt ctgaaactga    3180
taaagacggt aaagaatcta aggttgtgaa attccgttac ttcactaatg aaggtgtcat    3240
ggccaaaggt gttacggtta ttgatggttt cacacaatat tttggagaag acggtttcca    3300
agctaaagat aagttagtaa cctttaaagg taaaacttat tactttgacg cacacactgg    3360
taatggtatc aaggatactt ggagaaatat caatggtaag tggtactact ttgatgcaaa    3420
cggtgttgct gctacaggtg cacaagtcat caatggtcaa aaactttact caatgaaga    3480 tggaagccaa gttaaaggtg gcgttgttaa gaatgcagat ggtacttaca gcaagtacaa    3540
```

```
agaaggtttt ggagagctag tgactaacga attcttcaca actgatggca atgtttggta    3600
ctatgcaggc gctaatggta agactgttac aggtgcacaa gtcatcaatg gccaacacct    3660
atactttaat gcagacggaa gccaagttaa gggtggtgtt gttaagaatg cagatggtac    3720
ttatagtaag tataatgctt caacaggtga acgcttgact aatgagtttt tcacaacagg    3780
cgacaacaac tggtactaca ttggtgctaa tggtaagtca gtgactggtg aagttaaaat    3840
tggtgacgat acttatttct tcgctaagga tggtaaacaa gtaaaaggtc aaacagtaag    3900
tgctggcaat ggtcgaatta gctattacta tggtgatagt ggtaagagag ctgttagcac    3960
atggatagaa attcaaccag gagtttacgt ttactttgat aagaatggtc ttgcttatcc    4020
acctagagtg ctaaactaag actagatct                                      4049
```